US005883236A

United States Patent [19]

Hengeveld et al.

[11] Patent Number: 5,883,236

[45] Date of Patent: Mar. 16, 1999

[54] PROCESS FOR N-DESMETHYLATING ERYTHROMYCINS AND DERIVATIVES THEREOF

[75] Inventors: John E. Hengeveld, Kenosha, Wis.; Xiaoxing Dong, Lancaster, Pa.; Ashok K. Gupta, Gurnee, Ill.; Richard R. Copp, Jr., Kenosha, Wis.; Ramiya H. Premchandran, Gurnee, Ill.

[73] Assignee: Abbott Laboratories, Abbott Park, Ill.

[21] Appl. No.: 974,085

[22] Filed: Nov. 19, 1997

[51] Int. Cl.[6] .......... G07H 1/00

[52] U.S. Cl. .......... 536/7.2; 536/18.5

[58] Field of Search .......... 536/7.2, 18.5

[56] References Cited

U.S. PATENT DOCUMENTS 3,726,385 4/1973 Freeberg .

5,578,579 11/1996 Lartey et al. .

*Primary Examiner*—Elli Peselev

*Attorney, Agent, or Firm*—Portia Chen; Mona Anand

[57] ABSTRACT

Disclosed is an improved and efficient process for N-desmethylating the 3'-amino nitrogen of erythromycins and for converting the 3'-N-desmethylated erythromycins into 3'-N-substituted derivatives of 8,9-anhydro-erythromycin 6,9-hemiketals.

12 Claims, No Drawings

PROCESS FOR N-DESMETHYLATING ERYTHROMYCINS AND DERIVATIVES THEREOF

TECHNICAL FIELD

The present invention relates to an improved and efficient process for N-desmethylating the 3'-amino nitrogen of erythromycins and for preparing gastro-intestinal prokinetic erythromycin compounds thereof. More particularly, the invention relates to N-desmethylating the 3'-amino nitrogen of erythromycins by using 1-chloroethyl chloroformate and converting the 3'-N-desmethylated erythromycins into 3'-N-substituted derivatives of 8,9-anhydro- erythromycin 6,9-hemiketals

BACKGROUND OF THE INVENTION

Erythromycins A through D, represented by formula (E),

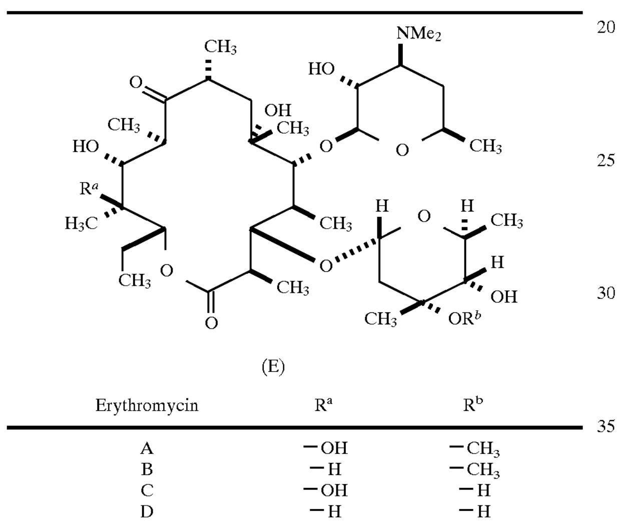

(E)

| Erythromycin | $R^a$ | $R^b$ |
|---|---|---|
| A | $-OH$ | $-CH_3$ |
| B | $-H$ | $-CH_3$ |
| C | $-OH$ | $-H$ |
| D | $-H$ | $-H$ |

are well-known and potent antibacterial agents, used widely to treat and prevent bacterial infection.

Some erythromycin derivatives having the formula I below possess an expected degree of prokinetic activity and are described in U.S. Pat. No. 5,578,579.

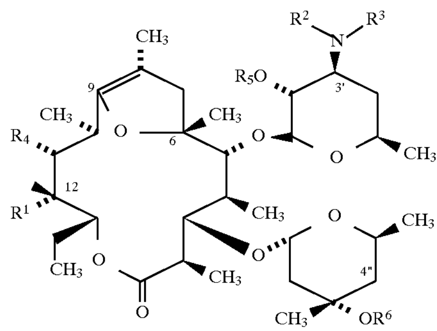

The preparation of these prokinetic compounds requires the preparation of the intermediate compounds, N-desmethyl-4"-deoxy-erythromycin A and N-desmethyl-4"-deoxy-erythromycin B.

One procedure for the preparation of N-desmethyl derivatives of various macrolide antibiotics has been described in U.S. Pat. No. 3,725,385, issued Apr. 3, 1973, which teaches that the methyl group may be removed by a one-step treatment with a single addition of iodine in a pH-adjusted solution from −10° C. to 50° C. The N-desmethylation step with iodine does not generally go to completion, leaving a substantial amount of the starting material with the final product.

There is, therefore, a need to provide an improved and more efficient process for the manufacture of the 3'-N-substituted derivatives of 8,9-anhydro-erythromycin-6,9-hemiketals.

SUMMARY OF THE INVENTION

The present invention relates to a process for preparing a compound having formula I:

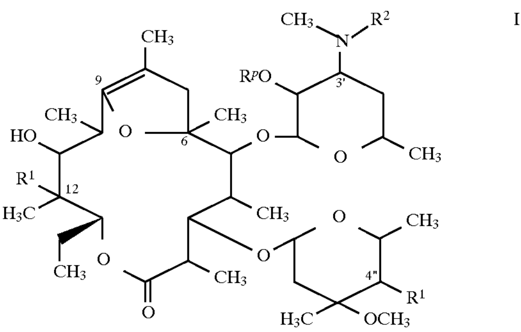

and pharmaceutically acceptable salts thereof. In formula I, $R^p$ is hydrogen or hydroxy-protecting group; $R^1$ is independently hydrogen or hydroxy at each occurrence; and $R^2$ is a loweralkyl. The method comprises the steps of:

(a) treating a compound represented by the formula:

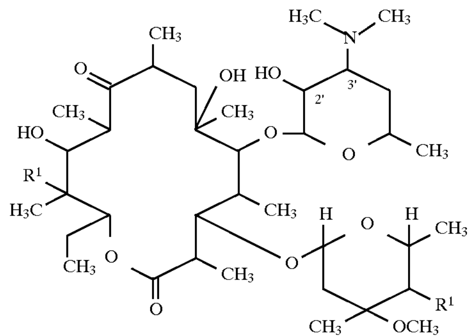

with a hydroxy-protecting group and 1-chloroethyl chloroformate to afford the compound of formula:

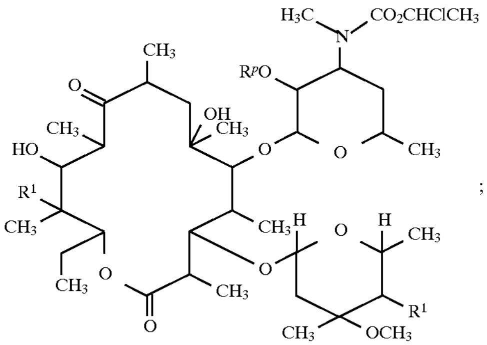

;

(b) heating the compound from step (a) with an alcohol to afford the compound of formula;

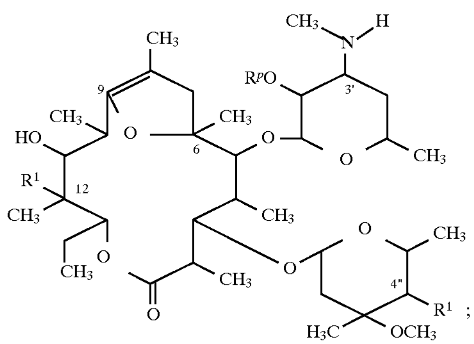

(c) alkylating the 3'-N with an alkylating agent in presence of a base.

The process of the invention is an efficient process in that it provides desmethylation and enol ether formation in one step. It is, therefore, more economical and cleaner than the processes known in the art.

DESCRIPTION OF THE INVENTION

The term "loweralkyl" as used herein refers to a $C_1$-to-$C_8$ straight or branched chain saturated hydrocarbon radical including, but not limited to, methyl, ethyl, n-propyl, isopropyl, n-butyl, sec-butyl, isobutyl, tert-butyl and the like.

By "pharmaceutically acceptable salts" is meant those acid addition salts of the compounds of Formula (I) which are, within the scope of sound medical judgement, suitable for use in contact with the tissues of humans and lower animals without undue toxicity, irritation, allergic response, and the like commensurate with a reasonable benefit/risk ratio, and which are effective for their intended use.

Pharmaceutically acceptable salts are well known in the art. For example, S. M. Berge, et al. describe pharmaceutically acceptable salts in detail in *J. Pharmaceutical Sciences* (1977), 66: 1–19. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic or by using other methods used in the art such as ion exchange. Other pharmaceutically acceptable salts include nitrate, bisulfate, borate, formate, butyrate, valerate, 3-phenylpropionate, camphorate, adipate, benzoate, oleate, palmitate, stearate, laurate, lactate, fumarate, ascorbate, aspartate, nicotinate, p-toluenesulfonate, camphorsulfonate, methanesulfonate, 2-hydroxyethanesulfonate, gluconate, glucoheptonate, lactobionate, glycerophosphate, pectinate, lauryl sulfate, alginate, cyclopentanepropionate, digluconate, dodecylsulfate, ethanesulfonate, hemisulfate, heptonate, hexanoate, 2-naphthalenesulfonate, pamoate, persulfate, pivalate, propionate, undecanoate salts and the like, and may be prepared according to conventional methods. Representative alkali or alkaline earth metal salts include sodium, calcium, potassium, magnesium salts and the like.

Scheme 1 illustrates the process of the invention for the preparation of the compounds of formula 1.

In accordance with Scheme 1, the 2'-hydroxy of erythromycin 1 is protected with a suitable hydroxy protecting reagent in an aprotic solvent, such as those described by T. W. Greene and P. G. M. Wuts in *Protective Groups in Organic Synthesis*, 2nd ed., John Wiley & Son, Inc., 1991. Hydroxy protecting reagents include, for example, acetic anhydride, benzoic anhydride, benzyl chloroformate, 1-chloroethyl chloroformate, hexamethyldisilazane, or a trialkylsilyl chloride in an aprotic solvent. Examples of aprotic solvents are dichloromethane, 1,2-dichloro ethane, chloroform, DMF, tetrahydrofuran (THF), N-methyl pyrrolidinone, dimethylsulfoxide, diethylsulfoxide, N,N-dimethylformaamide, N,N-dimethylacetamide, hexamethylphosphoric triamide, a mixture thereof or a mixture of one of these solvents with ether, tetrahydrofuran, 1,2-dimethoxyethane, acetonitrile, ethyl acetate, acetone and the like. Aprotic solvents do not adversely affect the reaction, and are preferably dichloromethane, 1,2-dichloroethane, chloroform, DMF, tetrahydrofuran TIF), N-methyl pyrrolidinone or a mixture thereof.

Preferably, the 2'-hydroxy group is acetylated by using acetic anhydride or acetyl chloride. Without the work up of the reaction mixture, the reaction mixture is treated with about 9 equivalents of 1-chloroethyl chloroformate. This reagent removes one of the two methyl groups on the 3'-nitrogen to afford N-chloroethyl carbamate compound 2. The reaction is carried out in a solvent selected from the group consisting of ethyl acetate, acetone, toluene, acetonitrile, methyl t-butyl ether, dimethoxyethane, and 1,2-dichloroethane. More preferred solvent is 1,2-dichloroethane since the product is more soluble in 1,2-dichloroethane than other solvents. Keeping the product in solution without resorting to huge solvent volumes makes the workup much easier. If it is desired to isolate the crystalline intermediate, solvent other than 1,2-dichloroethane can be used. The reaction is typically carried out at about 50° C.

The chloroethyl carbamate compound 2 is then converted into an enol ether compound 3 by heating with an alcohol such as methanol, ethanol, propanol and the like, at a temperature from about 20° C. to about 65° C. from about 2 to 12 hours. Preferably, the reaction temperature is from about 20° C. to about 40° C. The monomethylamine acetate enol ether 3 may be isolated and crystallized from ethyl acetate or any other suitable solvent as a solid. The compound 3 may not be isolated and the reaction mixture is treated with an allylating agent to effect alkylation of the 3'-N-desmethyl derivative.

Scheme 1

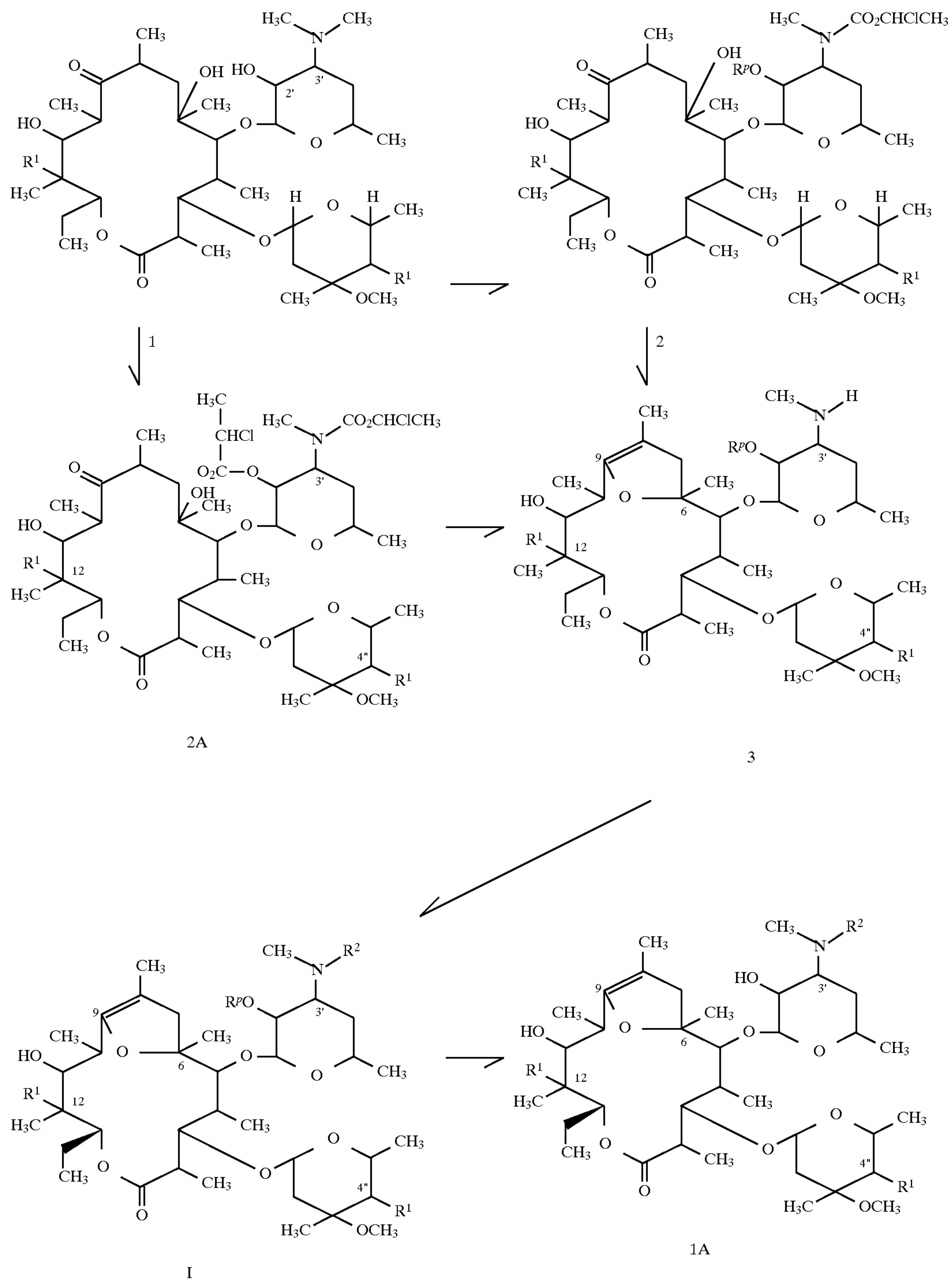

Compound 3 is alkylated using N-methylpyrrolidinone (NMP), acetonitrile, dimethylsulfoxide, or tetrahydrofuran as a solvent and an organic base such as a tertiary amine, as for example, diisopropylethylamine ((DIEA) or Hunig's base)) or an inorganic base such as sodium bicarbonate or potassium carbonate to afford a compound of formula I. The alkylating agents include, for example, alkyl halides, alkyl sulfates, alkyl sulfonates and the like. Preferably, the alkylating agent is selected from the group consisting of ethyl halides, ethyl sulfates and ethyl sulfonates. Most preferably, the alkylating agent is ethyl iodide. The 2'-hydroxy protected group in formula I is deprotected by the methods known in the art to obtain a compound of formula IA. It may be desirable to deprotect the 2'-hydroxy group of compound 2 before the alkylation step.

Alternatively, one may use 1-chloroethyl chloroformate to protect the 2'-hydroxy group and to effect the 3'-N-carbamoylation in one step to obtain 2'-chloroethyl carbonate-N-desmethyl-N-chloroethyl carbamate 2A. When this compound is heated with an alcohol, both chloroethyl carbonate and chloroethyl carbamate groups will be removed to afford 8,9-anhydro-6,9-hemiketal derivative 3, wherein $R^p$ is hydrogen. This process would be more efficient since the deprotection of the 2'-hydroxy and desmethylation of the 3'-nitrogen is obtained in one step.

Alternatively, as illustrated in Scheme 1A, Compound 2 may be desmethylated using an alcohol such as methanol, ethanol, propanol, isopropanol and the like, and an organic base such as a tertiary amine, as for example, diisopropylethylamine ((DIEA) or Hunig's base)) or an inorganic base such as sodium bicarbonate or potassium carbonate to afford a compound of formula 4. Compound 4 is alkylated in accordance with the procedure described above for Compound 3 to afford Compound 5. Compound 5 is heated in an organic solvent in the presence of an acid to afford a compound of formula I. The organic solvents include, for example, dimethyl formamide (DMF), alcohols such as ethanol, methanol, isopropanol and the like, acetonitrile, acetone, dioxane, and tetrahydrofuran. The acids used include hydrochloric acid, trifluoroacetic acid, dichloroacetic acid, sulfuric acid and the like. Preferably, the reaction is carried out using trifluoroacetic acid in DMF at 60° C. for about 12 to 24 hours.

Step 1: 2'-acetyl-4"-deoxy-3'-desmethyl-3'-N-((1-chloroethyl)carbamate)) erythromycin B To a 500 mL three neck flask was charged 20 g (28.5 mmol) 4"-deoxy Erythromycin B, available from Abbott Laboratories, 35.9 g (427.4 mmol, 15 equiv.) sodium bicarbonate, and 140 mL (7 mL/g) dichloroethane. The slurry was stirred at room temperature while 3.0 mL (31.3 mmol, 1.1 equiv.) acetic anhydride was added. The reaction was warmed to 50° C. and stirred for one hour. The reaction was sampled and checked for completion by Thin Layer Chromatography (TLC). Acetylation was complete. While continuing to stir the reaction mixture at 50° C. 21.5 mL (199.4 mmol, 7.0 equiv.) of 1-chloroethyl chloroformate was added dropwise. The reaction mixture exothermed to 54° C. during the early part of the addition then came back to 50° C. The reaction was sampled after one hour and checked for completion by TLC. Carbamylation was complete. After cooling the reaction in an ice/water bath the reaction was quenched with 200 mL 1.5N ammnonium hydroxide. The mixture was stirred for 30 minutes then settled and the top, wash layer removed. The organic layer was washed with 100 mL 1.5N ammonium hydroxide, then with 2×100 mL water. The dichloroethane solution was stripped down on the rotary evaporator to give 37.02 g of a thick oil. This was diluted with 100 mL heptane and the resulting solution stripped down to give 26.85 g of white solid.

Scheme 1A

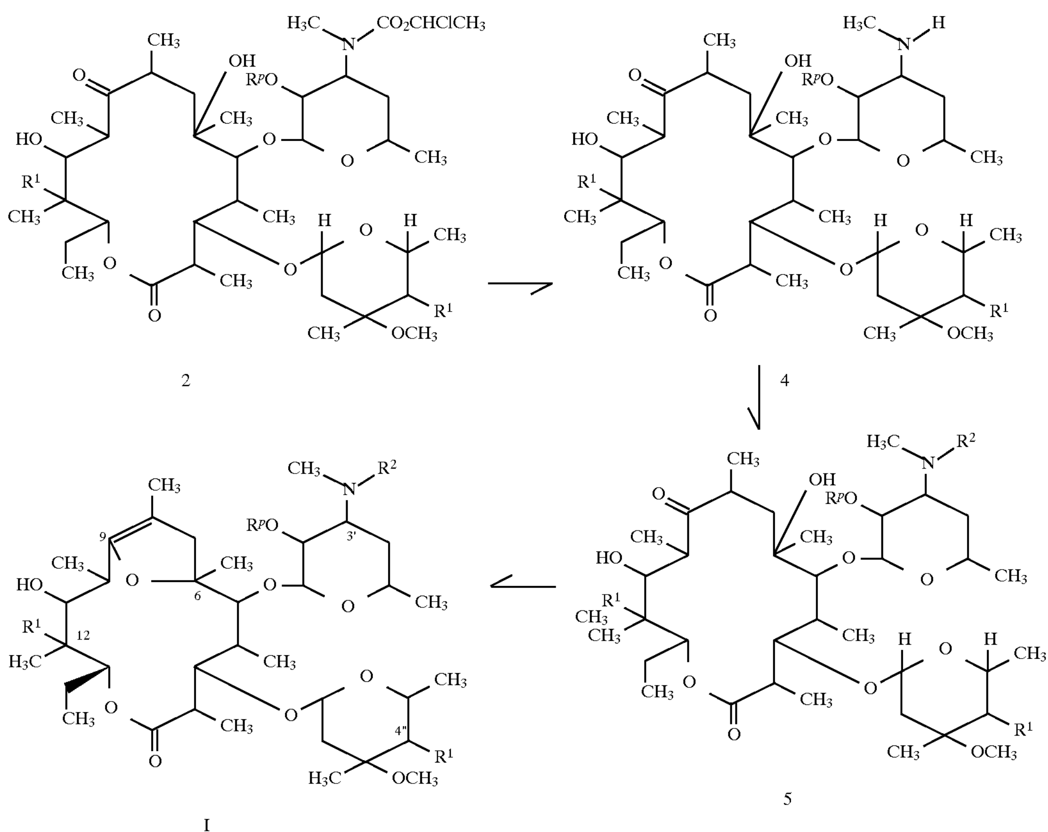

In a preferred embodiment, $R^1$ in formula I is hydrogen and $R^2$ is ethyl.

EXAMPLES

Example 1

8,9-anhydro-4"-deoxy-3'-N-desmethyl-3'-ethyl-erythromycin B-6,9-hemiketal (ABT-229)

Step 2: 8,9-anhydro-2'-acetyl-4"-deoxy-3'-N-desmethyl-erythromycin B-6,9-hemiketal The white solid obtained from the above step 1 was dissolved in 160 mL methanol and warmed to 40° C. The solid dissolved after approximately 30 minutes. The reaction was sampled and checked for completion after four hours at 40° C. The reaction was finished. The methanol was stripped off on the rotary evaporator to give 23.93 g of solid. This material was slurried in 100 mL heptane at 40° C. After stripping off the heptane the solid weighed 23.15 g.

Step 2A: 3'-N-desmethyl-4"-deoxy erythromycin B:

Alternatively, to a 500 mL round bottom flask containing 21 g of crude 2'-acetyl-4"-deoxy-3'-N-desmethyl-3'-N((1-chloroethyl)carbamate)) erythromycin B was charged 210 mL methanol and 13.4 mL (3.3 equiv.) diisopropylethylamine. The reaction mixture was warmed to 60° C. and stirred overnight, then cooled to room temperature. The methanol was stripped off on the rotary evaporator to give 22.7 g of a foam. The foam was dissolved in 250 mL toluene and concentrated on the rotary evaporator to produce a slurry. The solid was filtered, washed with 100 mL toluene and dried in a vacuum oven at 45° C. The dried product weighed 12.95 g.

The product thus obtained is ethylated as described in Step 3 below. The resulting 3-N-desmethyl-3'-N-ethyl-4"-deoxy erythromycin B is treated with an acid in the presence of an organic solvent to afford ABT-229 in accordance with Step 4 below.

Step 3: 8,9-anhydro-2'-acetyl-4"-deoxy-3'-N-desmethyl-3'-ethyl-erythromycin B-6,9-hemiketal The solid from Step 2 was dissolved in 60 mL N-Methyl pyrrolidinone (NMP) at 40° C. To this 40° C. solution was added 14.9 mL (85.5 mmol, 3.0 equiv.) Diisopropylethylamine and 6.8 mL (85.5 mmol, 3.0 equiv.) ethyl iodide. The reaction was stirred at 40° C. for four hours then overnight at room temperature. A sample was taken in the morning and checked for reaction completion. The reaction was finished. The reaction solution was diluted with 60 mL water and extracted with 2×200 mL heptane. The reaction was then extracted with 200 mL 10% ethyl acetate in heptane. The extracts were combined and back-extracted with 20 mL acetonitrile. The heptane solution was then washed with 2×100 mL water and 1×100 mL 10% aqueous ammonium chloride. The heptane solution was stripped down on the rotary evaporator to give 19.17 g of white solid.

Step 4: 8,9-anhydro-4"-deoxy-3'-N-desmethyl-3'-ethyl-erythromycin B-6,9-hemiketal (ABT-229)

The white solid from Step 3 was dissolved in 200 mL methanol. The resulting solution was warmed to 40° C. and stirred for 4 hours. It was then cooled to about 20° C. and stirred for the weekend. It was checked by TLC for completion on Monday morning. The reaction was finished. It was stripped down on the rotary evaporator to give 17.29 g of a white foam, the crude product ABT-229.

Example 2

8,9-anhydro-2'-acetyl-3 '-N-desmethyl-3'-ethyl-erythromycin B-6,9-hemiketal

Step 1: 2'-acetyl-3'-desmethyl-3'-N-((1-chloroethyl) carbamate)) erythromycin B

To a 500 ML three neck flask was charged 17.9 g (25.0 mmol) erythromycin B, available from Abbott Laboratories, 31.5 g (374.7 mmol, 15 equiv.) sodium bicarbonate, and 125 mL 1,2-dichloroethane. The mixture was heated to 45° C. and 2.8 mL (30.0 mmol, 1.2 equiv.) acetic anhydride was added. The reaction mixture was stirred for one hour and 15 minutes. The reaction was sampled and checked for completion by TLC. Acetylation was complete. While continuing to stir the reaction mixture at 45° C. 18.9 mL (174.9 mmol, 7.0 equiv.) of 1-chloroethyl chloroformate was added dropwise. The reaction mixture exothermed to 54° C. during the early part of the addition then came back to 50° C. The reaction was sampled after about 50 minutes and checked for completion by TLC. Carbamylation was complete. After cooling the reaction in an ice/water bath the reaction was quenched with 175 mL. 1.5N ammonium hydroxide, keeping the temperature of the mixture below 10° C. during the addition. The ice bath was removed and the mixture was stirred for 30 minutes. Another 100 mL of 1,2-dichloroethane was added and the mixture shaken. The mixture was then allowed to settle. The organic layer was washed with 100 mL 1.5N ammonium hydroxide, then with 2×100 mL water. The dichloroethane solution was stripped down on the rotary evaporator to give 24.9 g of white foam.

Step 2: 8,9-anhydro-2'-acetyl-3'-N-desmethyl-erythromycin B-6,9-hemiketal 10.9 g of the white foam obtained from the above step 1 was dissolved in 120 mL methanol and warmed to 40° C. The reaction mixture was maintained at that temperature for four hours. The reaction mixture was then allowed to stand overnight. The reaction was complete as determined by TLC. The methanol was stripped off on the rotary evaporator to give 10.48 g of solid. This solid was dissolved in 100 mL ethyl acetate, transferred to a separatory funnel and washed with 3×100 mL saturated aqueous $NaHCO_3$. About 50 mL of aqueous layer was drawn off. 100 mL water was added and the mixture shaken well. The ethyl acetate layer settled fairly well but the aqueous layer contained a lot of white solid. The mixture was filtered and the ethyl acetate layer separated from the aqueous layer in the filtrate. The ethyl acetate layer was concentrated to about 20 mL white slurry and filtered. The total solid weighed 9.47 g.

Step 3: 8,9-anhydro-2'-acetyl-3'-N-desmethyl-3'-ethyl-erythromycin B-6,9-hemiketal The solid from Step 2 was dissolved in 56 mL N-Methyl pyrrolidinone (NMP). To this solution was added 2.8 mL (16.0 mmol, 1.25 equiv.) Diisopropylethylamine and 1.3 mL (16.0 mmol, 1.25 equiv.) ethyl iodide. The reaction was stirred at 40° C. for four hours then at room temperature for the weekend. A sample was checked by TLC indicating that the reaction has gone to completion. The reaction mixture was transferred to a separatory funnel with ethyl acetate. The reaction solution was diluted with 100 mL ethylacetate and washed with 100 mL water. The aqueous layer was extracted with 50 mL ethyl acetate. The extracts were combined and washed with 2×100 mL water. The solvent was stripped down on the rotary evaporator to give 9.14 g of foam.

It is understood that the foregoing detailed description and accompanying examples are merely illustrative and are not to be taken as limitations upon the scope of the invention, which is defined solely by the appended claims and their equivalents. Various changes and modification to the disclosed embodiments will be apparent to those skilled in the art. Such changes and modification, including without limitation those relating to the chemical structures, stereochemistry, substituents, derivatives, intermediates, syntheses, formulations and/or methods of use of the invention, may be made without departing from the spirit and scope thereof.

We claim:

1. A process for preparing a compound represented by formula:

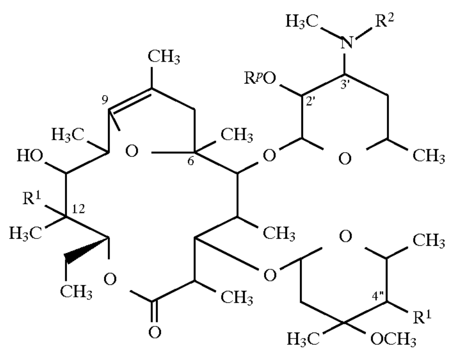

or a pharmaceutically acceptable salt thereof, wherein $R^p$ is hydrogen or hydroxy-protecting group;

$R^1$ is independently hydrogen or hydroxy at each occurrence; and $R^2$ is loweralkyl;

the method comprising the steps of:

(a) treating a compound represented by the formula:

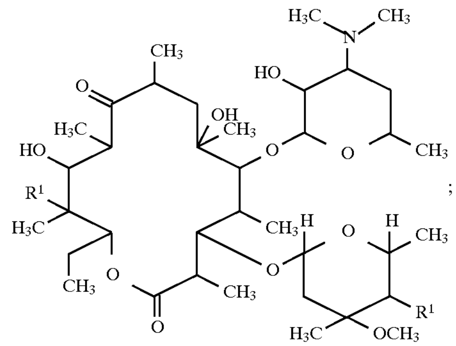

with a hydroxy-protecting group and 1-chloroethyl chloroformate in a solvent to afford the compound of formula:

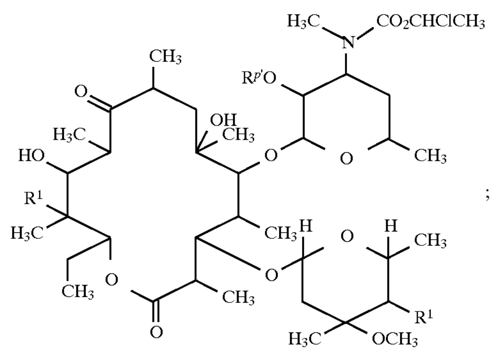

wherein Rp' is a hydroxy-protecting group;

(b) heating the compound from step (a) with an alcohol to afford the compound of formula:

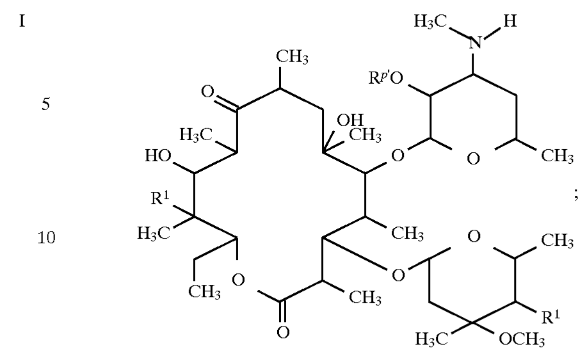

(c) alkylating the 3'-N with an alkylating agent in the presence of base.

2. The process of claim 1, wherein the 2'-protected hydroxy group of the compound in step (b) is deprotected before alkylation in step (c).

3. The process of claim 1, wherein the 2'-protected hydroxy group of compound is deprotected after alkylation in step (c).

4. The process of claim 1, wherein $R^1$ is hydrogen.

5. The process of claim 1 wherein the alkylating agent is selected from the group consisting of alkyl halides, alkyl sulfates and alkyl sulfonates.

6. The process of claim 1, wherein the alkylating agent is ethyliodide.

7. The process of claim 1, wherein the solvent in step (a) is selected from the group consisting of acetone, ethyl acetate, toluene, acetonitrile, methyl t-butyl ether, dimethoxyethane and dichloroethane.

8. The process of claim 7, wherein the solvent is 1,2-dichloroethane.

9. The process of claim 1, wherein the temperature of the reaction mixture in step (a) is from about 20° C. to about 65° C.

10. The process of claim 1, wherein the solvent in step (c) N-methylpyrrolidinone, dimethylsulfoxide, tetrahydrofuran or acetonitrile and the base is $NaHCO_3$, $K_2CO_3$, or diisopropylethylamine.

11. The process of claim 1, wherein the compound of formula I is 8,9-anhydro-4"-deoxy-3'-N-desmethyl-3'-N-ethyl erythromycin B-6,9-hemiketal.

12. A process for preparing a compound represented by formula:

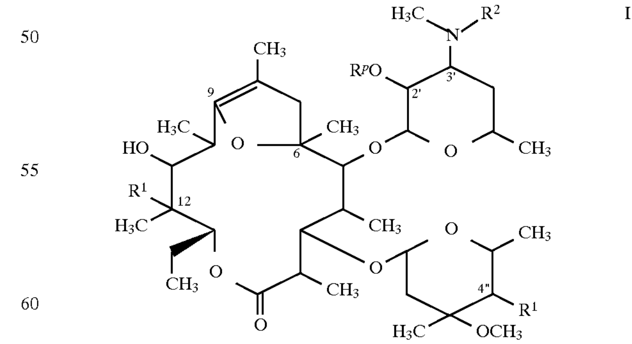

or a pharmaceutically acceptable salt thereof, wherein $R^p$ is hydrogen or hydroxy-protecting group;

$R^1$ is independently hydrogen or hydroxy at each occurrence; and $R^2$ is loweralkyl;

the method comprising the steps of:

(a) treating a compound represented by the formula:

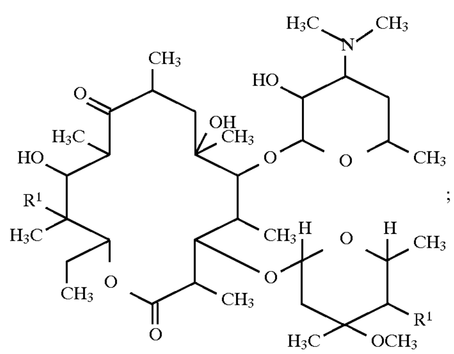

with a hydroxy-protecting group and 1-chloroethyl chloroformate in a solvent to afford the compound of formula:

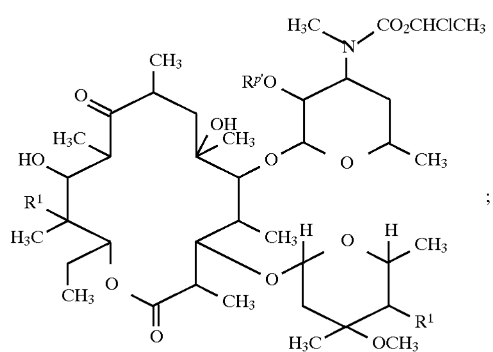

wherein Rp' is a hydroxy-protecting group;

(b) treating the compound obtained in step (a) with a base in an organic solvent to afford a compound of formula:

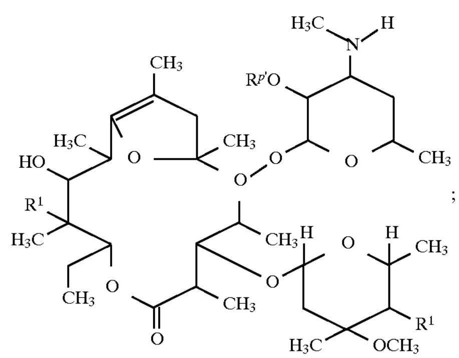

(c) alkylating the compound obtained in step (b) in the presence of a base to obtain a compound of formula:

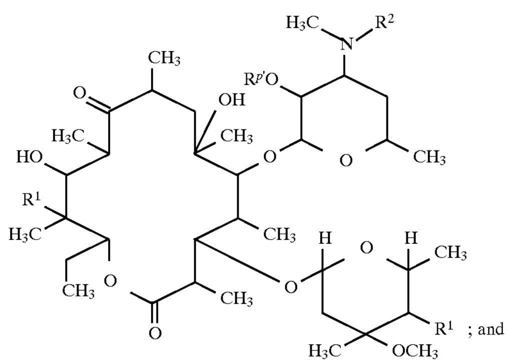

(d) heating the compound obtained in step (c) in an organic solvent in the presence of an acid to obtain a compound of formula I.

* * * * *